United States Patent
Unver et al.

(10) Patent No.: US 11,065,148 B2
(45) Date of Patent: Jul. 20, 2021

(54) HEAT EXCHANGER CAP

(71) Applicant: Paxman Coolers Limited, Huddersfield (GB)

(72) Inventors: Ertugrul Unver, Bradford (GB); Glenn Alan Paxman, Holmfirth (GB); Neil Eric Paxman, Holmfirth (GB)

(73) Assignee: PAXMAN COOLERS LIMITED, Huddersfield (GB)

( * ) Notice: Subject to any disclaimer, the term of this patent is extended or adjusted under 35 U.S.C. 154(b) by 483 days.

(21) Appl. No.: 15/512,745

(22) PCT Filed: Sep. 22, 2015

(86) PCT No.: PCT/GB2015/052740
§ 371 (c)(1),
(2) Date: Mar. 20, 2017

(87) PCT Pub. No.: WO2016/046535
PCT Pub. Date: Mar. 31, 2016

(65) Prior Publication Data
US 2017/0239083 A1    Aug. 24, 2017

(30) Foreign Application Priority Data
Sep. 23, 2014 (GB) .................................... 1416757

(51) Int. Cl.
*A61F 7/02* (2006.01)
*A61F 7/00* (2006.01)
*A61F 7/10* (2006.01)

(52) U.S. Cl.
CPC .................. *A61F 7/02* (2013.01); *A61F 7/10* (2013.01); *A61F 2007/0008* (2013.01);
(Continued)

(58) Field of Classification Search
CPC ...... A61F 2007/0008; A61F 2007/0056; A61F 2007/0098; A61F 2007/0233; A61F 7/2007; A61F 7/02
See application file for complete search history.

(56) References Cited

U.S. PATENT DOCUMENTS

| 1,404,320 A | 1/1922 | Roberts et al. |
| 1,896,953 A | 2/1933 | Hassell |

(Continued)

FOREIGN PATENT DOCUMENTS

| CN | 2406636 Y | * 11/2000 | ............... A61F 7/00 |
| CN | 2406636 Y | 11/2000 | |

(Continued)

*Primary Examiner* — Linda C Dvorak
*Assistant Examiner* — Annabeth E Rodriguez
(74) *Attorney, Agent, or Firm* — Coats & Bennett, PLLC

(57) ABSTRACT

A heat exchanger cap, and method of manufacture of a heat exchanger cap configured to conform to a human head the cap comprising a first element for covering one side of the head; a second element for covering the other side of the head; and an intermediate joining element joined to, and which spaces apart, the first element and second element. Each of the elements define a single passageway for the passage of fluid through the cap. Each of the elements are provided with a flow interface in the region where the elements are joined. The flow interface defines an inlet for the passage of fluid into the passageway of one of the elements, and an outlet for the passage of fluid from the passageway out of the same element.

10 Claims, 8 Drawing Sheets

(52) U.S. Cl.
CPC .......... *A61F 2007/0056* (2013.01); *A61F 2007/0098* (2013.01); *A61F 2007/0233* (2013.01)

(56) References Cited

U.S. PATENT DOCUMENTS

| | | | |
|---|---|---|---|
| 2,726,658 | A | 12/1955 | Chessey |
| 3,242,245 | A | 3/1966 | Greig et al. |
| 3,256,565 | A | 6/1966 | Alesi et al. |
| 3,867,939 | A | 2/1975 | Moore et al. |
| 4,566,455 | A | 1/1986 | Kramer |
| 4,987,896 | A | 1/1991 | Nakamatsu |
| 5,086,771 | A | 2/1992 | Molloy |
| 5,169,384 | A | 12/1992 | Bosniak et al. |
| 5,342,411 | A | 8/1994 | Maxted et al. |
| 5,469,579 | A | 11/1995 | Tremblay et al. |
| 5,603,728 | A | 2/1997 | Pachys |
| 5,630,230 | A | 5/1997 | Fujino et al. |
| 5,802,865 | A | 9/1998 | Strauss |
| 5,871,526 | A * | 2/1999 | Gibbs ............. A61F 7/02 607/104 |
| 5,895,418 | A | 4/1999 | Saringer |
| 5,950,234 | A | 9/1999 | Leong et al. |
| 6,117,164 | A | 9/2000 | Gildersleeve et al. |
| 6,156,059 | A | 12/2000 | Olofsson |
| 6,178,562 | B1 | 1/2001 | Elkins |
| 6,312,453 | B1 * | 11/2001 | Stefanile ........... A61F 7/10 607/108 |
| 6,375,674 | B1 | 4/2002 | Carson |
| 6,427,467 | B1 | 8/2002 | Bell |
| 6,681,590 | B1 | 1/2004 | Jones |
| 7,721,349 | B1 | 5/2010 | Strauss |
| 2002/0058976 | A1 | 5/2002 | Lee |
| 2002/0091431 | A1 | 7/2002 | Gunn et al. |
| 2003/0088299 | A1 | 5/2003 | Magers et al. |
| 2005/0028551 | A1 | 2/2005 | Noda et al. |
| 2005/0107855 | A1 | 5/2005 | Lennox et al. |
| 2005/0132468 | A1 | 6/2005 | Lundgren |
| 2005/0187502 | A1 * | 8/2005 | Krempel ........... A61F 7/02 602/5 |
| 2006/0235496 | A1 | 10/2006 | Collins et al. |
| 2008/0184456 | A1 | 8/2008 | Fontanez |
| 2008/0228248 | A1 | 9/2008 | Guyuron et al. |
| 2008/0269852 | A1 | 10/2008 | Lennox et al. |
| 2009/0054958 | A1 | 2/2009 | Nofzinger |
| 2010/0030306 | A1 * | 2/2010 | Edelman ........... A61F 7/02 607/104 |
| 2010/0095641 | A1 | 4/2010 | Ruetenik |
| 2010/0186436 | A1 | 7/2010 | Stormby |
| 2010/0319110 | A1 | 12/2010 | Preston-Powers |
| 2012/0283534 | A1 | 11/2012 | Carr et al. |
| 2013/0138185 | A1 | 5/2013 | Paxman et al. |
| 2013/0226044 | A1 | 8/2013 | Moore et al. |
| 2014/0046410 | A1 * | 2/2014 | Wyatt ............. A61F 7/10 607/104 |
| 2014/0172050 | A1 | 6/2014 | Dabrowiak |
| 2014/0222121 | A1 | 8/2014 | Spence et al. |
| 2014/0276253 | A1 | 9/2014 | Varga et al. |
| 2014/0277302 | A1 | 9/2014 | Weber et al. |
| 2016/0354232 | A1 * | 12/2016 | Rozental ........... A61F 7/10 |

FOREIGN PATENT DOCUMENTS

| | | |
|---|---|---|
| DE | 1454922 A1 | 4/1969 |
| DE | 102011100616 A1 | 11/2011 |
| EP | 1520568 A1 | 4/2005 |
| GB | 2323915 A | 10/1998 |
| GB | 2482792 A | 2/2012 |
| JP | 05278081 A | 10/1993 |
| JP | 2002316357 A | 10/2002 |
| KR | 20070088224 | 8/2007 |
| WO | 0038601 A1 | 7/2000 |
| WO | 0162193 A2 | 8/2001 |
| WO | 0200132 A1 | 1/2002 |
| WO | 2006110405 A2 | 10/2006 |
| WO | 0003666 A1 | 1/2013 |
| WO | 2013074128 A2 | 5/2013 |
| WO | 2013190333 A2 | 12/2013 |

\* cited by examiner

HEAT EXCHANGER CAP

The present disclosure relates to a heat exchanger cap.

In particular the disclosure is concerned with a heat exchanger cap configured to conform to a human head.

BACKGROUND

Various medical treatments involve the cooling of a body part. In the treatment of cancer, it is known to cool the head of a patient during chemotherapy in order to reduce the extent and/or likelihood of hair loss.

Shown in FIG. 1 is an example of a known cooling cap 10. The cooling cap 10 comprises a single tube 12 in a concentric hoop arrangement, stacked on top of itself, to form a part spherical garment to be worn on a patient's head. The tube 12 has a fluid inlet 14 and a fluid outlet 16. In use, coolant is pumped from the inlet 14 to the outlet 16 to thereby remove heat from a contact area with the patient.

The cap 10 is formed by wrapping the tube 12 around the outside of a dome shaped former and gluing sides of the tube 12 to one another, which is time consuming.

Such a cap 10 may be provided in a number of sizes, but inevitably a cap is going to be "oversize" for a patient. Additionally, heads are (generally) not dome shaped, and individual's heads do not even have the same relative proportions when compared to one another. Hence in order to seek to achieve good levels of thermal conduction, and hence heat transfer, between the patient and the cap 10, the cap must be drawn in towards the patient's head to make contact with the patient. FIG. 2 shows an outline of the cap 10 as viewed from above. In a non-deformed state the cap 10 has a first shape, as shown by the continuous black line. If the patient's head is narrower than this, having for example the width of the oval shape shown by the dotted line, then when the cap 10 is drawn in to fit to the side of a patient's head, the front 18 and rear 20 of the cap will be pushed away from their original position, as shown by the discontinuous dotted line in FIG. 2. Also the top of the cap will be urged away from the top surface of the patients head. This creates a gap between the head of the patient and the cap 10 at the front, back and/or top of the cap. Hence the patient's head will not be cooled adequately in those regions, and the patient will not benefit from the cooling treatment.

Hence a heat exchanger cap which is configured such that it more consistently conforms to a patient's head, and which deforms to a lesser extent when fitted to the patient, is highly desirable.

SUMMARY

According to the present invention there is provided an apparatus and method of manufacture as set forth in the appended claims. Other features of the invention will be apparent from the dependent claims, and the description which follows.

Accordingly there may be provided a heat exchanger cap configured to conform to a human head the cap comprising: a first element for covering one side of the head; a second element for covering the other side of the head; and an intermediate joining element joined to, and which spaces apart, the first element and second element; each of the elements defining a single passageway for the passage of fluid through the cap; each of the elements being provided with a flow interface in the region where the elements are joined; the flow interface defining an inlet for the passage of fluid into the passageway of one of the elements, and an outlet for the passage of fluid from the passageway out of the same element.

The intermediate joining element may be provided with a main inlet for the passage of fluid into the cap, and a main outlet for the passage of fluid out of the cap wherein the main inlet defines the beginning of the single passageway and the main outlet defines the end of the single passageway.

The side elements may be configured to conform to the temple, parietal, and side regions of the head.

The intermediate element may be configured to conform to the top, crown and nape of the head.

Each of the interface regions of the first and second elements may be provided in an abutment wall which extends along one side of the element and describes an arc extending from a location corresponding to the temple and parietal regions to the nape region of their respective side of the head, the intermediate element having an abutment wall on two sides along its length, each of the intermediate element abutment walls configured for abutment with one of the first or second element abutment walls, the abutment walls and element geometry being configured such that, when the abutment walls are fixed together the elements are biased towards defining a predetermined cap geometry which is resistant to distortion.

The passageway may have a boustrophedonic route in at least one region between the main cap inlet and main cap outlet.

The boustrophedonic route of the passageway may be aligned with the direction from the nominal front of the cap to the nominal back of the cap.

The passageway may have a boustrophedonic route in each of the elements, and the boustrophedonic route is aligned with the direction from the nominal front of the cap to the nominal back of the cap.

One or more of the elements may be divided into regions, the passageway in at least one region having a boustrophedonic route.

The passageway may have a boustrophedonic route throughout the majority of the elements of the cap, the route extending from the main cap inlet to the main cap outlet.

There may also be provided a method of manufacture of a heat exchanger cap configured to conform to a human head comprising the steps of: providing a first pair of formers which define the shape of a first element of the cap for covering the parietal, side and temple regions on one side of the head; providing a second pair of formers which define the shape of a second element of the cap for covering the parietal, side and temple regions on the other side of the head; providing a third pair of formers which define the shape of an intermediate joining element for covering the top and crown of the head linking one former of each pair of formers together to define a surface which corresponds to a nominal outer surface of the cap; and linking the other former of each pair of formers together to define a surface which corresponds to a nominal inner surface of the cap.

A plurality of pairs of intermediate joining element formers may be provided which are interchangeable with each other and each pair of intermediate joining element formers have a different width, such that the first and second pair of formers in combination with the plurality of intermediate joining element formers define cap forming surfaces of different sizes to thereby define cap shapes of different sizes the method comprising the step of determining which of the pairs of intermediate joining element formers to use in combination with the first and second pair of formers, dependent upon the size of the cap to be manufactured.

The method may further comprise the steps of providing: a plurality of sheet materials between the pair of linked formers; and bringing together the linked formers such that the first material sheet and second material sheet are brought into contact to undergo a joining process.

Each former may be provided with a surface pattern which defines the cross sectional shape of the cap; the method further comprising the step of when the linked formers are together, at least partially evacuating the internal passageways of the former thereby force the first and second sheet materials towards the walls of the formers, thereby deforming the sheet materials to the shape of the former to thereby form the elements of the cap having the desired external cross sectional shape.

Advantage

Hence there is provided a heat exchanger cap which is structured to define a head shape, and structured so that elements of the cap may be drawn towards the patient's head without significant biasing of the other elements of the cap away from the patients head. This has the advantage that the cap will provide a closer fit, and hence conform to a larger percentage of the patient's head than the cap of the related art.

There is also provided a method of manufacture of a heat exchanger cap using a set formers which can be assembled in different combinations to enable the manufacture of different sized caps without the need for providing a whole former unit for each size of cap. This simplifies the manufacture of different sized caps, and hence increases the speed with which different size caps may be produced, and hence also reduces the cost which they can be produced for.

BRIEF DESCRIPTION OF THE DRAWINGS

Examples of the present disclosure will now be described with reference to the accompanying drawings, in which.

DETAILED DESCRIPTION

Figure 1:
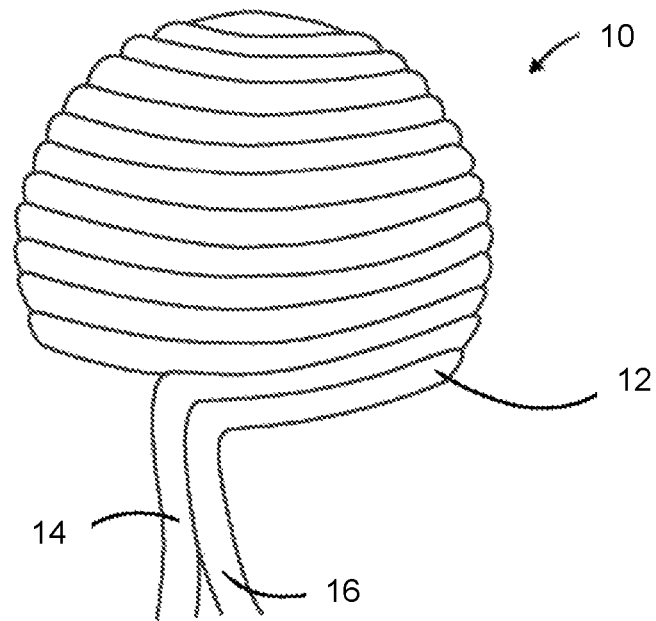
FIGS. 1 and 2 show an example of the related art.
Figure 2:
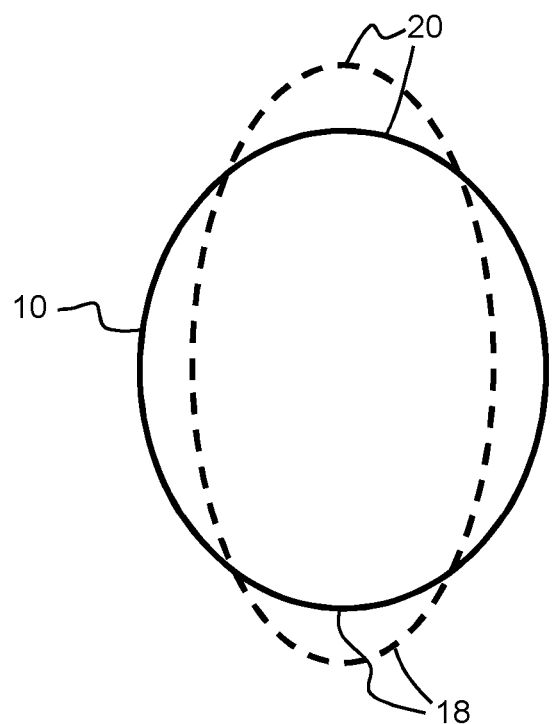
Figure 3:
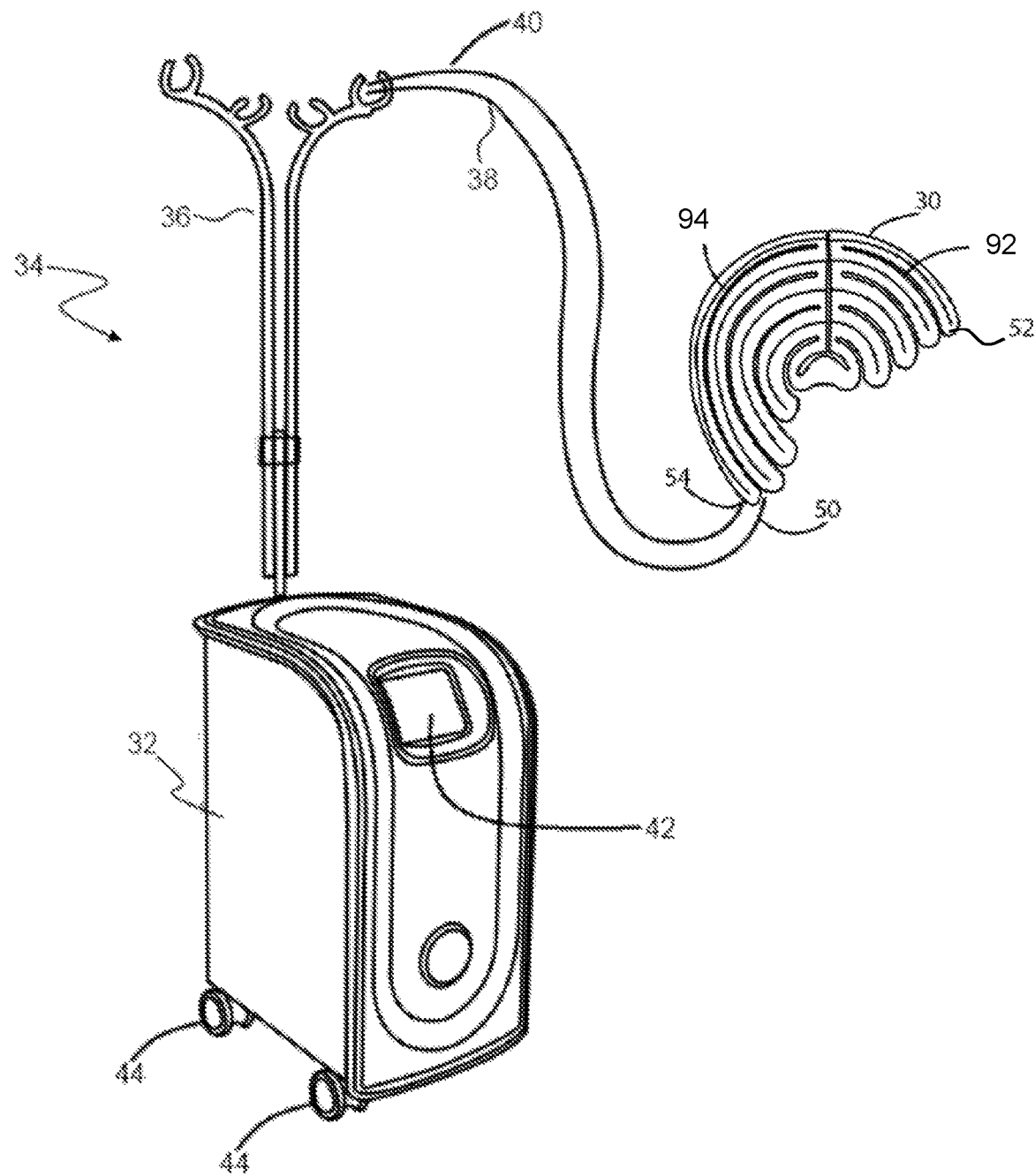
FIG. 3 shows a heat exchanger cap of the present disclosure in combination with a system for the control and flow of heat regulation fluid through the cap.

FIG. 3 shows an example of a heat exchanger cap 30 in combination with a fluid flow and temperature control unit 32 to form a fluid temperature control regulation system 34. A stand frame 36 for the support of fluid supply and return tubes 38, 40 extends from the control unit 32. The tube 38 delivers temperature regulation fluid (that is to say, a heat transfer fluid) to the cap 30. The tube 40 receives the same temperature regulation fluid from the cap 30. The control unit 32 is controllable by a user via an interface panel 42, which may also present information relevant to the operation of the system 34. The control unit 32 is provided with rollers 44 such that it is easily transportable.

In operation, a user operates the system 34 to regulate a patient's head to a desired temperature. In particular, the system is configured for cooling a patient, and in such examples the temperature regulation fluid will be a coolant. In other examples the system 34 may be configured to heat or maintain the body temperature of the patient. Regulation of the fluid flow rate, and temperature of the temperature regulation fluid to achieve a desired heat transfer rate, thereby bringing the patient's temperature to the desired level, are controlled in dependence upon the users input requirements. The fluid is pumped via the delivery tube 38 to an inlet 50 to the cap 30. The fluid then passes through a single passageway 52 provided in the cap 30, and exits the cap 30 at an outlet 54 (hidden from view in FIG. 3) to enter the return tube 40, and hence re-enter the system 34 to be brought back to the required temperature.

The shape, form and constituent elements of the cap will be now be described with reference to FIGS. 4 to 8.

Figure 4:
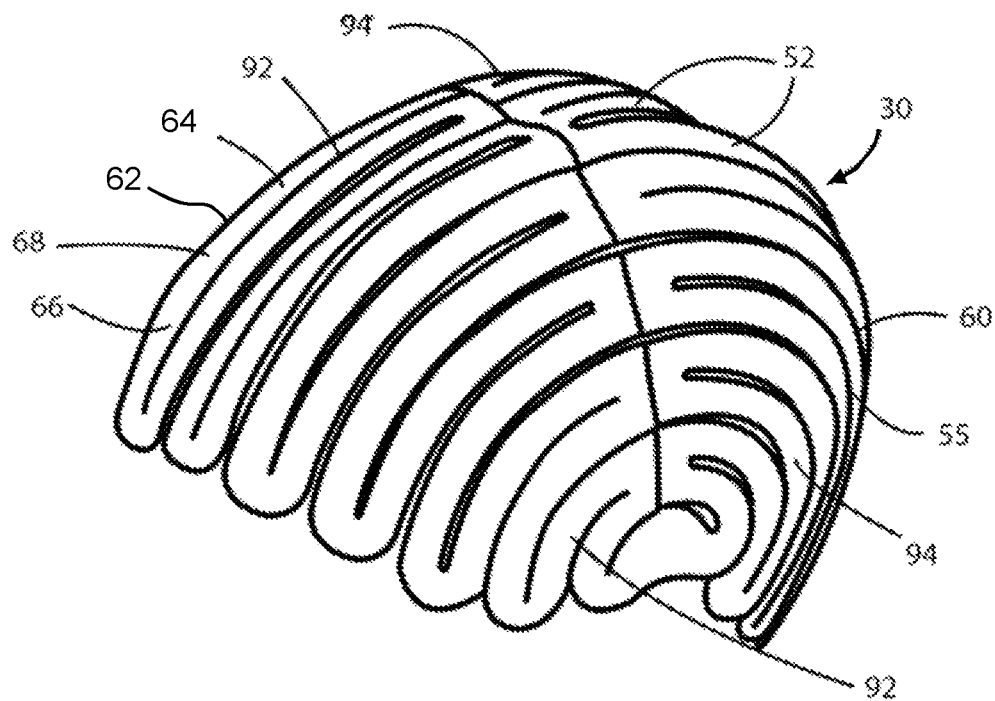
FIG. 4 shows a view of elements of the heat exchanger cap of the present disclosure joined together and fitted to a patient's head.
Figure 5:
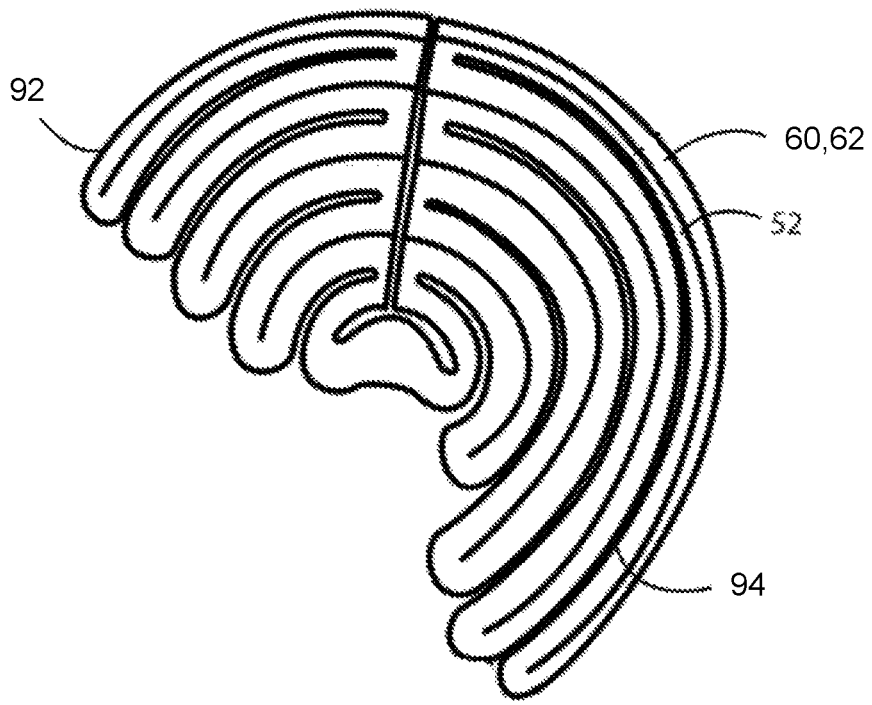
FIG. 5 shows a side view of a first and second element of the heat exchanger cap.
Figure 6:
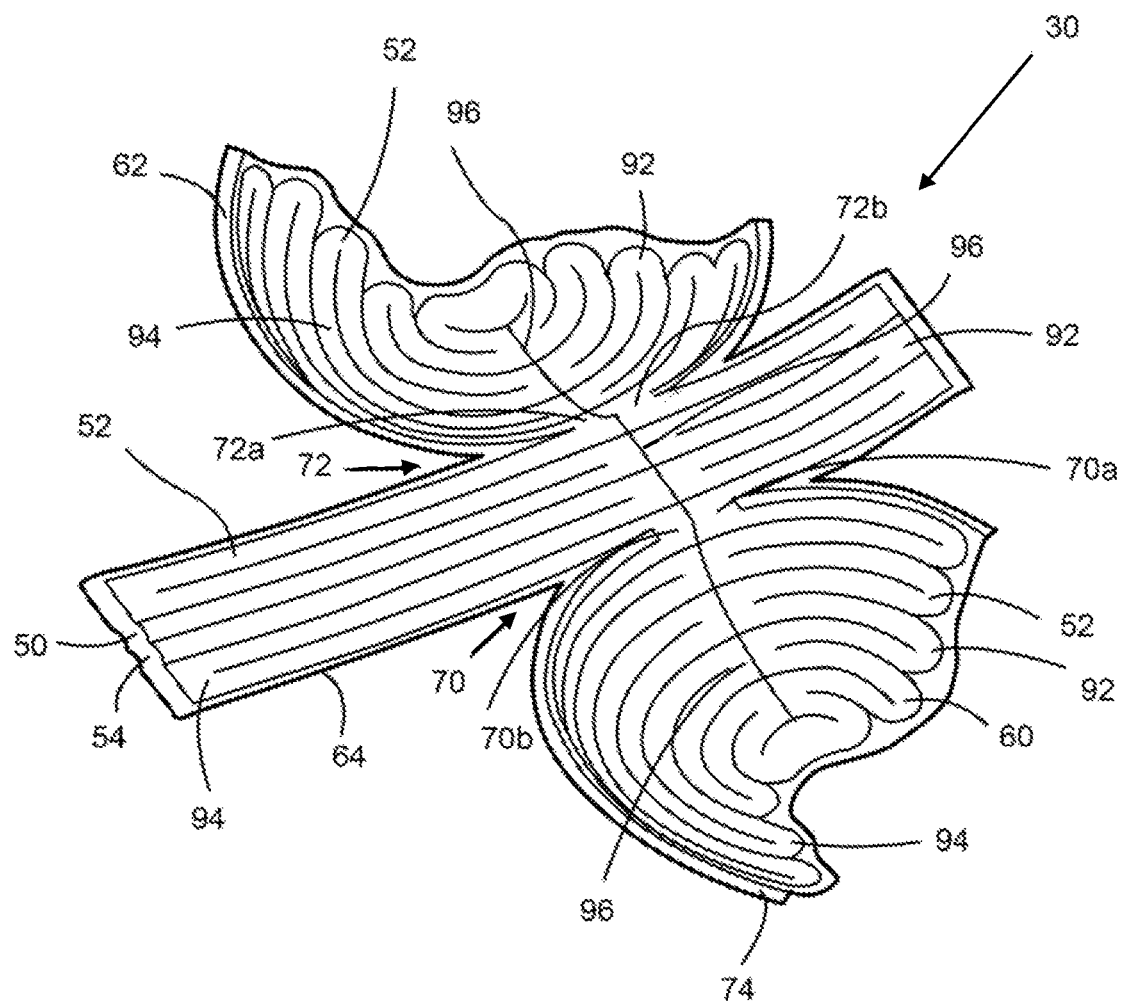
FIG. 6 shows a perspective view of elements of the cap prior to the elements being brought together to form a cap shape.
Figure 7:
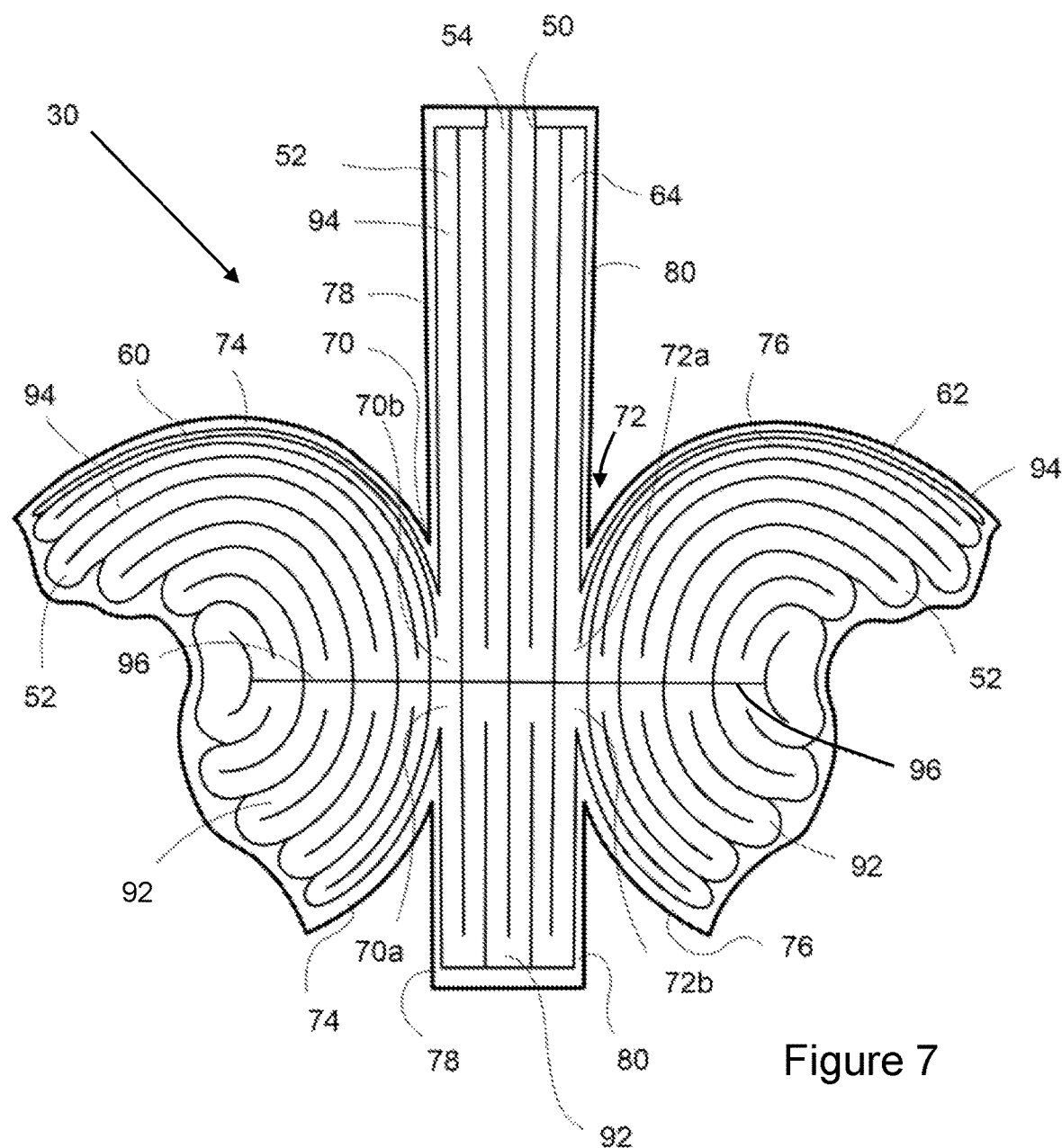
FIG. 7 shows a plan view of the cap elements shown in FIG. 6.
Figure 8:
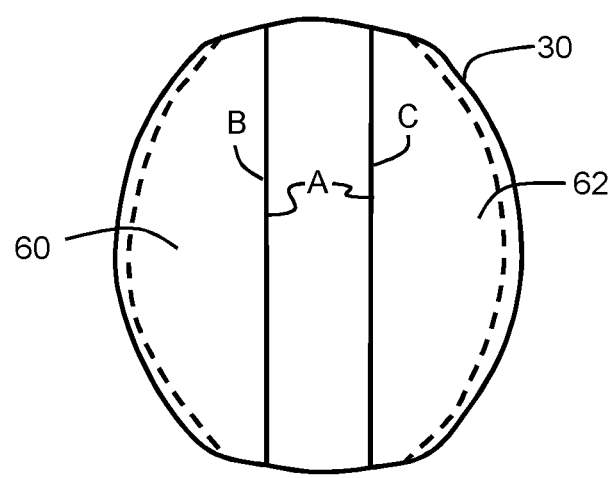
FIG. 8 shows an outline of a plan view of the heat exchanger cap of the present disclosure in a non-deformed and deformed state.

FIG. 4 shows a perspective view of cap 30 of the present disclosure. FIG. 5 shows a side view of the first or second element 60, 62 in isolation from the intermediate element 64. FIG. 6 shows a perspective view of the elements 60, 62, 64 in a partially exploded view, and in a state which the cap will have during manufacture. FIG. 7 shows a plan view of the same arrangement of FIG. 6. FIG. 8 shows a plan view of the cap in an assembled state, with some detail removed for clarity.

It will be appreciated that the views presented show only one example of how the essential features may be configured, and is not necessarily representative of what the cap will look like in practice.

The cap 30 comprises a first element 60 for covering one side of the head, a second element 62 for covering the other side of the head, and an intermediate joining element 64 for covering the top of the head. That is to say, the first and second (side) elements 60, 62 are configured to cover, and conform to, at least one of the temple, parietal and side regions of the head. The intermediate element 64 is configured to cover, and conform to, at least one of the top, crown and nape of the head.

The intermediate joining element 64 is joined to, and spaces apart, the first element and second element. Each of the elements 60, 62, 64 define a section of the single passageway 52 through the cap 30 for the passage of temperature regulation fluid. That is to say, each of the elements 60,62,64 define the single passageway 52 for the passage of fluid throughout the entire cap.

Each of the elements 60,62,64 are provided with a flow interface 70,72 in the region where the elements 60,62,64 are joined. Each flow interface 70,72 defines an inlet 70a, 72a for the passage of fluid into the passageway of one of the side elements 60,62 from the intermediate element 64, and an outlet 70b,72b for the passage of fluid from the passageway out of the same element 60,62 into the intermediate element 64.

That is to say, and as shown in FIGS. 6,7 the intermediate joining element 64 is joined to the first side element 60 at a flow interface 70, and the intermediate joining element 64 is joined to the second side element 62 at a flow interface 72. Flow interface 70 comprises and inlet 70a and an outlet 70b. Flow interface 72 comprises and inlet 72a and an outlet 72b.

The cap comprising the elements 60, 62, 64 may be provided as a combination of joined layer materials, spaced apart in the regions which define the passageways 52, and joined in the regions between the passageways 52. However, the elements may be manufactured by any appropriate method, being made from any number of parts or formed integrally as one piece. In other examples, the cap 30 may be provided as a layer of material having a unified construction. An example of a method of manufacture is described later.

The intermediate joining element 64 is provided with a main inlet 50 for the passage of fluid into the cap, and a main outlet 54 for the passage of fluid out of the cap, as shown in FIGS. 6,7. The main inlet 50 defines the beginning of the single passageway 52 and the main outlet defines the end of the single passageway 52.

Although the cap is described as having a single inlet 50, and a single outlet 54, the inlet and outlet may comprise a number of apertures and sub-structures. However, there is provided only one entrance (inlet) region to the passageway of the cap, regardless of how that inlet may be provided and/or configured. Likewise there is provided only one outlet region from the cap, however that outlet may be provided or configured.

The intermediate element 64 is generally elongate and rectangular in appearance.

Each of the interface regions 70,72 of the first and second elements 60,62 are provided in an abutment wall 74,76 which extends along one side of the elements 60,62 and describes an arc extending from a location corresponding to the temple and parietal regions to the nape region of their respective side of the head.

The intermediate element 64 is provided with an abutment wall 78,80 on each of its two sides along its length. Each of the intermediate element abutment walls 78,80 are configured for abutment with one of the first or second element abutment walls 74,76. That is to say the first element abutment wall 74 is configured for abutment with the intermediate element abutment wall 78, and the second element abutment wall 76 is configured for abutment with the intermediate element abutment wall 80, as shown in FIGS. 6, 7.

That is to say, the abutment walls 74,76 of the first and second elements 60, 62 describe an arc extending from a location on the element 60, 62 corresponding to the temple and parietal regions to the nape region on their respective side of the head. The shape and location of the abutment walls 74,76,78,80 and the geometry (i.e. shapes) of the elements 60, 62, 64 are configured such that, when the elements 60, 62, 64 are joined together along their abutment walls 74,76,78,80, the resultant cap closely approximates the shape of a human head. Additionally, by virtue of the presence of a join along their abutment walls 74,76,78,80, the elements 60, 62, 64 are biased towards defining a predetermined cap geometry which is resistant to distortion. Put another away, the provision of a join, where the interface regions meet, allows the majority of each element to move and flex without substantially affecting the element it is joined to. The join effectively provides a flexible framework which defines a flexible head shaped structure, with the side and top (i.e. intermediate) elements being able to flex and move relative to the framework without influencing or causing significant movement of another element.

The join may be provided by an adhesive or by applying heat and/or pressure to the abutment wall is such that they are bonded to one another along their length. The abutment walls may be spot welded to one another. Materials akin to Velcro may be applied to the surface of the abutment walls to hold them together. Bands or straps may additionally or alternatively be provided on the cap elements 60,62,64 to bring the abutment walls into abutment and hold them in a fixed relationship.

Thus there may be provided a cap 30 as shown in FIG. 4 or FIG. 8 in which the first element 60 and second element 62 are joined to the intermediate element 64. The inlets 70a, 72a and outlets 70b, 72c of each element 60, 62, 64 are aligned such that the outlet from one element is aligned with the inlet of another element to thereby define the single passageway 52 throughout the cap 30. In FIG. 8 the detail of the route of the passageway 52 is omitted. In the other figures the route of the single passageway 52 through the first element 60, second element 62 and intermediate element 64 is representational of an example of the device of the present disclosure, although other configurations may be provided. The outer layer of the cap 30 may be provided with a cover thereby insulating and hiding the outward external surface of the material defining the passageway 52.

In at least one region of the cap, the passageway 52 has a boustrophedonic route between the main cap inlet 50 and main cap outlet 54. The boustrophedonic route of the passageway 52 is back and forth aligned with a direction from the nominal front of the cap 60 towards the nominal back of the cap 60. That is to say, as shown in FIGS. 4 to 7, the passageway 52 has a serpentine route having a turning point at the nominal front of the cap which corresponds to the front of the head upon which it sits, and a turning point along a line aligned with direction between the front and back of the head at a point between the front and back of the head. As shown in the figures, the passageway 52 has a boustrophedonic, or serpentine, route in each of the elements 60, 62, 64, the boustrophedonic route being aligned with the direction from the nominal front of the cap to the nominal back of the cap, with a turning point at approximately halfway between the front and back of the cap which abuts another turning point which is the leading end of another backwards and forwards run of the passageway.

In the example shown, the passageway 52 has a boustrophedonic/serpentine route throughout the majority of the elements making up the cap, the boustrophedonic route extending from the main cap inlet 50 to the main cap outlet 54.

One or more of the elements 60, 62, 64 may be divided into flow regions. For example, with reference to any of the elements 60, 62, 64 shown in FIGS. 4 to 7, there may be provided a first flow region 92 and a second flow region 94 where the passageway 52 is arranged to have a local pattern to correspond to specific to a part of the head. The passageway 52 in at least one of the regions (for example regions 92, 94) have a boustrophedonic/serpentine route. In the example shown in the figures, the local pattern in region 92 is defined by the forward and backward route of the passageway 52 over substantially the nominal front half of the side of the cap 30, which corresponds to the nominal front half of the side of the head on which it will be worn. The second region 94 defines a backwards and forwards serpentine passageway route which covers the nominal back half of the side of the cap 30, and hence the nominal back half of the head on which the cap 30 will be worn. Put another way, the flow regions 92,94 may define a volume of the cap 30 in which the passageway 52 extends only part of the way, and not the whole of the way, from the front to the back of the cap 30. Likewise the intermediate element 64 may comprise region where the route of the passageway from back to front of the element is truncated such that it is also divided into flow regions 92, 94 as shown in the Figures.

Regional variations in the patterns of passageway 52 (such as the regions 92,94) may be provided to focus temperature regulation (for example cooling) in particular locations on a human head which commonly have specific temperature characteristics. For example, where regions of the human head are known to be generally warmer than other regions, then the passageway 52 may be provided in those regions to provide a different heat transfer rate between the cap and the head. For example, there will be a region of different heat transfer rate (compared to the other regions of the passageway 52) along the line of the junction 96 between the regions 92,94.

In the examples shown, the passageway 52 has a substantially constant cross-sectional area along its length, from inlet 50 to outlet 54. Additionally, the passageway 52 has a substantially constant cross-sectional shape along its length, from inlet 50 to outlet 54.

In other examples, the cross-sectional area of the passageway 52 may vary in size and shape along its length.

Figure 9:
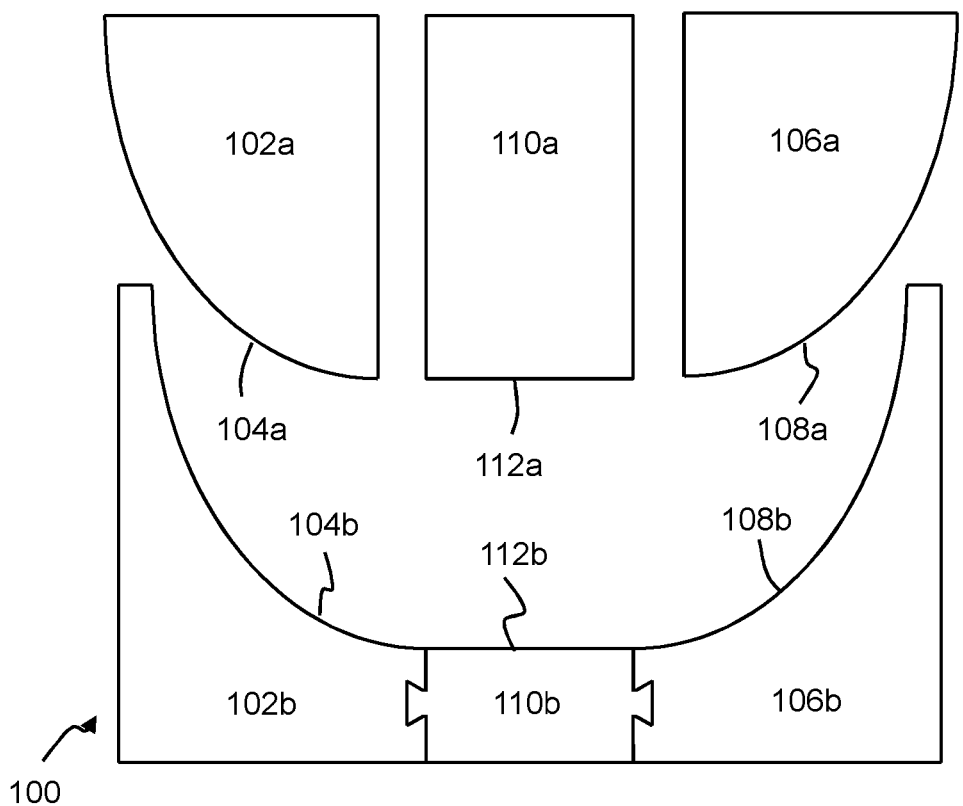
FIG. 9 shows a cross sectional part exploded view of elements of a forming tool used to form the elements of the cap.
Figure 10:
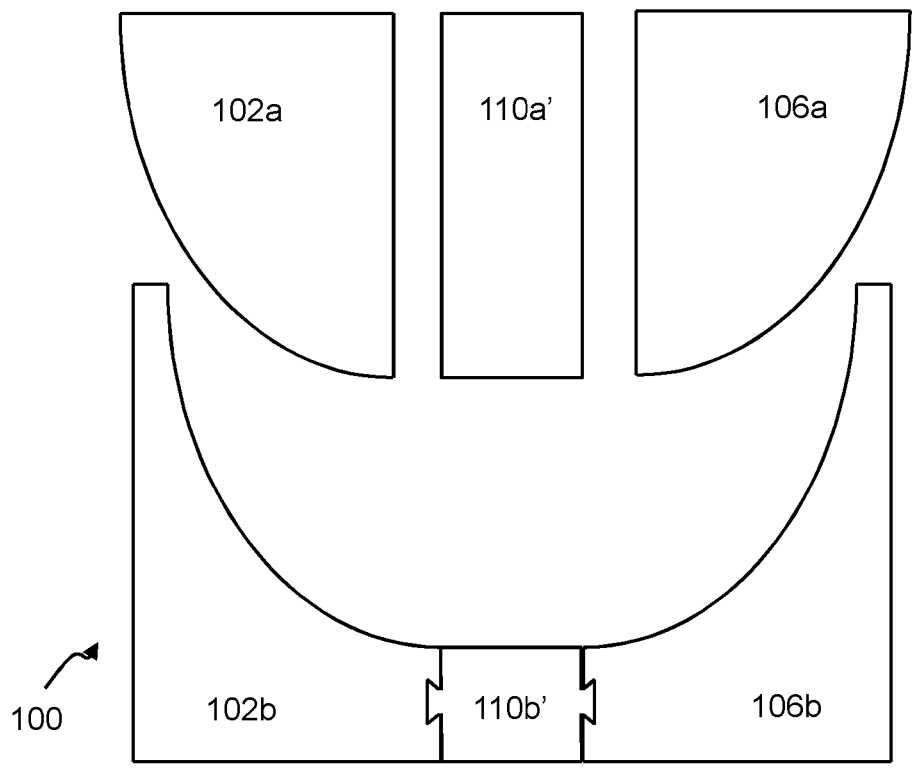
FIG. 10 shows a different combination of elements to that shown in FIG. 9.
Figure 11:
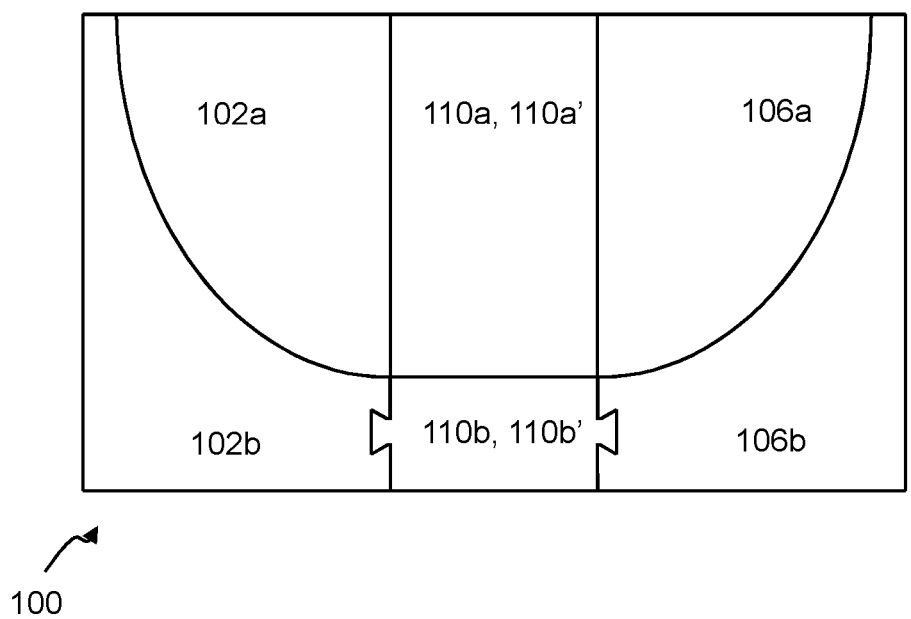
FIG. 11 shows the elements of the forming tool of FIGS. 9, 10 in an assembled configuration.

The elements are made using a former 100 which defines the geometry of the first, second and intermediate elements 60, 62, 64. A diagrammatic cross sectional view of a former arrangement is shown in FIGS. 9, 10, 11.

The former 100 is provided in three parts out of three pairs of formers 102, 106, 110.

A first pair of formers 102*a*, 102*b* is provided which define the shape of the first element 60 of the cap 30 for covering the parietal, side and temple regions on one side of the head. The first pair of formers 102*a*, 102*b* are provided with forming surfaces 104*a*, 104*b* which define the geometry of the inner and outer surfaces of the first element 60. As can be seen in FIG. 9, the first pair of formers 102*a*,102*b* define a three-dimensional curved shape.

A first pair of formers 106*a*, 106*b* is provided which define the shape of the second element 62 of the cap 30 for covering the parietal, side and temple regions on the other side of the head. The second pair of formers 106*a*, 106*b* are provided with forming surfaces 108*a*, 108*b* which define the geometry of the inner and outer surfaces of the second element 62. As can be seen in FIG. 9, the second pair of formers 106*a*,106*b* define a three-dimensional curved shape.

A third pair of formers 110*a*, 110*b* is provided which define the shape of the intermediate joining element 64 for covering the top and crown of the head. The third pair of formers 110*a*, 110*b* are provided with forming surfaces 112*a*, 112*b* which define the geometry of the inner and outer surfaces of the third element 64. As can be seen in FIG. 9, the third pair of formers 110*a*,110*b* define a substantially flat shape.

One former of each pair of formers are linked together to define a surface which corresponds to a nominal outer surface of the cap 30. For example, as shown in FIG. 9, the lower half of the formers, 102*b*, 106*b*, 110*b* are linked together to provide a shape defining surface comprising forming surfaces 104*b*, 108*b*, 112*b*. The other former of each pair of formers is also linked together to define a surface which corresponds to a nominal inner surface of the cap 30. That is to say the upper half of the formers, 102*a*, 106*a*, 110*a* are linked together to provide a shape defining surface comprising forming surfaces 104*a*, 108*a*, 112*a*.

As part of the former assembly, there is provided a plurality of pairs of intermediate joining element formers 110*a*, 110*b* which are interchangeable with each other. Each pair of intermediate joining element formers 110*a*, 110*b* have a different width.

For example, the intermediate joining element formers 110*a*, 110*b* shown in FIG. 9 has a first width. An alternative intermediate pair of joining element formers 110*a*', 110*b*' are shown in FIG. 10 which have a second width, which is narrower (i.e. less than) the first width.

This provides a collection of former parts in which the first and second pair of formers 102,106 in combination with the plurality of intermediate joining element formers 110, 110', define cap forming surfaces of different sizes to thereby define cap shapes of different sizes. Hence the method comprising the step of choosing one of the pairs of intermediate joining element formers 110, 110' dependent upon the size of the cap to be manufactured.

That is to say, the region of the former which defines the an intermediate joining element may be interchangeable with any one of a number of intermediate elements, each having a different width, thereby providing a method for producing caps of different sizes.

Put another way, an intermediate element former of different sizes (namely different widths) can be combined with first, second element formers to provide caps having different sizes/dimensions.

The manufacture of a cap 30 may thus involve the step of selecting first and second and intermediate element formers appropriate to the size and shape of a patients head. For example, a first and second element former size choice may be made, which may be joined to an intermediate element former having a first size, second size, or third size etc. which are all different to each other.

The method of manufacture further comprises the step of sandwiching a sheet of a first material next to a sheet of a second material such that a first sheet separates the linked formers 102*a*, 106*a*, 110*a*/110*a*' from the second sheet, and the second sheet separates the linked formers 102*b*, 106*b*, 110*b*/110*b*' from the first sheet.

The method further comprises the step of executing a joining process including bringing the two halves of the linked formers together (as shown in FIG. 11) such that the first material sheet and second material sheet are brought into contact to undergo a joining process.

The joining process comprises bringing the material layers together at ambient conditions, that is to say in the absence of an elevated temperature. This can be achieved if the first sheet material and second sheet material comprise a silicone rubber having material properties which cause it to bond under the influence of pressure. Hence, it will only bond at the regions of the former which are in contact. The forming surfaces 104*a*, 104*b*, 108*a*, 108*b*, 112*a*,112*b* are provided with shoulders and ridges which define the pattern of the defining walls of the single passageway 52 and abutment walls 74, 76, 78, 80, for example as shown in FIGS. 6,7 and as described above. The sheet materials are not bonded in the "open" regions which define the passageway 52.

When the formers halves are pressed together, and the regions of the sheets are bonded, the internal passageways defined by the former surfaces 104*a*, 104*b*, 108*a*, 108*b*, 112*a*,112*b* are at least partially evacuated to thereby force (or "suck") the first and second sheet materials towards the walls of the formers 102*a*, 102*b*, 106*a*, 106*b*, 110*a*, 110*b* thereby deforming the sheet materials to the shape of the former and thereby provide the sheets with the desired external cross-sectional shape to produce the joined elements 60,62,64 a passageway 52 as shown in FIGS. 6,7.

As can be seen from FIGS. 6, 7 the product of the joining process is a precursor to the cap 30, where first and second elements 60, 62 are joined to the intermediate element 64 only at the joining regions 70, 72. The abutment walls 74, 76, 78, 80 are free of one another.

That is to say, the elements of the cap may be formed as one in one forming operation where at the conclusion of the forming operation, the elements of the cap are only joined at their flow interface region 70, 72. The abutment walls 74, 76, 78, 80 of the caps still require to be joined to form a cap by one of any number of methods may be adjustably joined, temporality joined or permanently joined, as described above.

It will be appreciated that the former assembly 100 shown in FIGS. 9 to 11 show merely a cross-sectional view of the required former shape, the cross section being one at a region somewhere in the region of the junction line 96 as shown in FIGS. 6, 7. With reference to FIG. 9, as one moves into or out of the page, the profile of the former pairs 102, 106, 110 will vary to define the shape of the cap precursor as shown in FIGS. 6, 7.

Although once complete the cap 30 cannot be modified in size, the manufacturing process lends itself to providing a wider range of better fitting caps than those of the related art.

Hence a well fitting cap of different sizes can be manufactured without re-configuration, or re-design, of the side elements formers 102,106. The intermediate element former 110,110', of simpler design, can be easily designed and manufactured in different sizes without need for fundamental redesign, except for a choice of number of lengths of the passageway 52. Hence a cap of different sizes may be more readily specified and manufactured, to meet the requirements of a number of different head sizes.

Thus manufacturing the cap 30 from a number of elements, rather than manufacturing the cap as a single element, allows for a greater variety of sizes of cap, and hence a cap of appropriate size and shape for a particular patient to be produced and made available as required.

As briefly discussed previously, FIG. 8 shows a plan view of the perimeter of the cap 30 when the abutment walls 74,76,78,80 of the elements 60, 62, 64 have been brought together, by whatever means. The continuous black line shows the boundary of the cap 30 when not in use or when fitted to a first size of head.

The dotted line shows the outside of the boundary of the cap 30 when fitted to a narrower head. A fabric or other layer material may be provided as a cover to the cap 30. A means for tightening may also be provided around the outside of the elements 60,62,64 to help draw the cap against the wearers head, thereby providing more uniform contact between the inside of the cap 30 and the treatment area.

Since the first and second element 60, 62 are joined by an intermediate element 64 on abutment walls 74,76,78,80 which extend from the nominal front of the head to the nominal back or nape of the head, this forms a head shaped structure. The join, or seam, where the abutment walls 74,76,78,80 meet allows the majority of each element 60, 62, 64 to move and flex without substantially affecting the element it is joined to. Hence internal surfaces of the cap are less likely to become spaced apart from the wearer's head when the cap is worn. For example, as shown in FIG. 8, when the cap 30 is fitted to a head slightly narrower in diameter than the nominal size of the cap, as shown by the dotted line, the sides of the cap may be drawn in without distorting or significantly moving the front and rear portions of the cap away from the wearer's head. Likewise the top of the cap 30 is less inclined to distort upwards away from the head.

Thus there is provided a cap, and method of manufacture of a cap, for cooling a human head which closely approximates the shape of a human head, and is thus a better fit. Additionally, by virtue of the elemental construction of the cap of the present disclosure, the cap is less inclined to become spaced apart from the user's head when one or more elements of the cap is urged (that is to say, tightened) against the head. Thus there is provided a comfortable and effective temperature regulation cap.

While the cap has been discussed in terms of a device to be employed during chemotherapy, it may also be employed as a cooling device for drivers (e.g. racing car drivers) and pilots of military aircraft and the like, where a helmet is worn by a user and it is desirable that the users head be kept to a comfortable temperature in order to help maintain their concentration. It may also be used to prevent sweat developing which can get into the users eyes causing discomfort and/or temporary loss of vision which in high speed applications could be especially effective in reducing risk of accident.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A heat exchanger cap configured to conform to a human head, the cap comprising:
    a first element for covering one side of the head;
    a second element for covering the other side of the head; and
    an intermediate joining element joined to and which spaces apart the first element and second element, the intermediate joining element having a length measured between a front and a back and also having a width, the width being substantially constant along the length;
    the intermediate joining element extending outward beyond two sides of the first and second elements;
    each of the elements defining a single passageway for the passage of fluid through the cap;
    each of the elements being provided with a flow interface in the region where the elements are joined;

the flow interface defining an inlet for the passage of fluid into the passageway of one of the elements, and an outlet for the passage of the fluid from the passageway out of the same element; and in at least the first element and the second element the single passageway defines flow regions on both sides of a junction line with each of the flow regions extending along just a portion of the cap with the portions located on opposing sides of the junction line, the passageway in each of the flow regions of the first and second elements comprising a boustrophedonic route aligned in a direction from back to front of the first and second elements.

2. The heat exchanger cap as claimed in claim 1, wherein the intermediate joining element is provided with a main inlet for the passage of fluid into the cap, and a main outlet for the passage of fluid out of the cap, wherein the main inlet defines a beginning of the single passageway and the main outlet defines an end of the single passageway.

3. The heat exchanger cap as claimed in claim 1, wherein the side elements are configured to conform to a temple, parietal, and side regions of the head.

4. The heat exchanger cap as claimed in claim 1, wherein the intermediate element is configured to conform to a top, crown and nape of the head.

5. The heat exchanger cap as claimed in claim 1, wherein:

each of the interface regions of the first and second elements are provided in an abutment wall which extends along one side of the respective first or second element and describes an arc extending from a location corresponding to a temple and parietal regions to a nape region of their respective side of the head; and the intermediate element having an abutment wall on two sides along the length, each of the intermediate element abutment walls configured to abut with one of the first or second element abutment walls;

the abutment walls and the first and second elements having a geometry configured such that, when the abutment walls are fixed together the first and second elements are biased towards defining a predetermined cap geometry which is resistant to distortion.

6. A heat exchanger cap configured to conform to a human head, the cap comprising:

a first element for covering one side of the head;

a second element for covering the other side of the head; and an intermediate joining element joined to and which spaces apart the first element and second element and which has a substantially constant width, the intermediate element extending outward beyond the first and second elements on both a nominal front and a nominal back of the cap;

each of the elements defining a single passageway for the passage of fluid through the cap with the passageway comprising a cap inlet to receive the fluid and a cap outlet to which the fluid is emitted;

each of the elements being provided with a flow interface in the region where the elements are joined;

the flow interface defining an inlet for the passage of fluid into the passageway of one of the elements, and an outlet for the passage of the fluid from the passageway out of the same element;

the passageway has a boustrophedonic route in each of the elements, and the boustrophedonic route is aligned with a direction from the nominal front of the cap to the nominal back of the cap.

7. The heat exchanger cap of claim 6, wherein the passageway comprises a substantially constant shape between the cap inlet and the cap outlet.

8. A heat exchanger cap configured to conform to a human head, the cap comprising:

a first element to cover one side of the head;

a second element to cover the other side of the head; and an intermediate joining element that covers a top side of the head, the intermediate joining element is positioned between and spaces apart the first element and second element and comprises a first abutment wall that extends along a first lateral side and a second abutment wall that extends along a second lateral side, the intermediate joining element comprising a substantially constant width measured between the first and second abutment walls;

the first abutment wall connected to the first element along a first joint and the second abutment wall connected to the second element along a second joint, each of the first and second joints comprises a forward section and a rear section;

the intermediate joining element extending outward beyond the first and second elements at both a nominal front and a nominal back of the cap;

each of the elements defining a single passageway for the passage of fluid through the cap;

a first flow interface positioned between the forward and rear sections of the first joint and the second flow interface positioned between the forward and rear sections of the second joint, each of the first and second flow interfaces comprising an inlet for the passage of fluid into the passageway of the respective element from the intermediate joining element and an outlet for the passage of the fluid from the respective element into the intermediate joining element;

the passageway has a boustrophedonic route in each of the elements that is aligned with a direction from the nominal front of the cap to the nominal back of the cap.

9. The heat exchanger cap of claim 8, wherein the first and second joints comprise spot welds.

10. The heat exchanger cap of claim 8, wherein the first and second joints permanently join the elements together.

* * * * *